(12) United States Patent
Umemoto et al.

(10) Patent No.: US 8,063,207 B2
(45) Date of Patent: Nov. 22, 2011

(54) MOLECULAR ASSEMBLY

(75) Inventors: Kazuhiko Umemoto, Aichi (JP); Hisato Takeuchi, Chita (JP); Hiroshi Nakamura, Seto (JP); Arimitsu Usuki, Nagoya (JP); Makoto Fujita, Chiba (JP)

(73) Assignees: Kabushiki Kaisha Toyota Chuo Kenkyusho, Aichi (JP); The University of Tokyo, Tokyo (JP)

( * ) Notice: Subject to any disclaimer, the term of this patent is extended or adjusted under 35 U.S.C. 154(b) by 584 days.

(21) Appl. No.: 12/237,795

(22) Filed: Sep. 25, 2008

(65) Prior Publication Data

US 2009/0082563 A1   Mar. 26, 2009

(30) Foreign Application Priority Data

Sep. 26, 2007 (JP) .................. 2007-249926

(51) Int. Cl.
*C07F 9/80* (2006.01)
*C07F 15/00* (2006.01)
(52) U.S. Cl. .......................... 544/181; 546/2
(58) Field of Classification Search .................. 544/181; 546/2
See application file for complete search history.

(56) References Cited

FOREIGN PATENT DOCUMENTS

| JP | A-2002-216845 | 8/2002 |
|---|---|---|
| JP | A-2002-239358 | 8/2002 |
| JP | A-2005-320392 | 11/2005 |

OTHER PUBLICATIONS

Yoshizawa et al., Science, vol. 312, pp. 251-254 (2006).*
Ibukuro et al., J. Am. Chem. Soc., vol. 120, No. 33, pp. 8561-8562 (1998).*
Paul et al., Heteroatom Chemistry, vol. 13, No. 6, pp. 567-573 (2002).*
Selby et al., Acc. Chem. Res., vol. 36, No. 12, pp. 933-944 (2003).*
Kusukawa et al., "Encapsulation of Large, Neutral Molecules in a Self-Assembled Nanocage Incorporating Six Palladium(II) Ions," *Agnew. Chemistry International Edition*, 1998, vol. 37, No. 22, pp. 3142-3144.
Ziegler et al., "Stabilization of a Reactive Cationic Species by Supramolecular Encapsulation," *Agnew. Chemistry International Edition*, 2000, vol. 39, No. 22, pp. 4119-4121.

* cited by examiner

*Primary Examiner* — Porfirio Nazario Gonzalez
(74) *Attorney, Agent, or Firm* — Oliff & Berridge, PLC

(57) ABSTRACT

A molecular assembly comprising a host metal complex with a space formed therein, and compounds having substituents enclosed in the metal complex within the space and molecular chains bonded to the substituents and extending to the exterior of the metal complex, wherein two or more substituents are enclosed in the same space of the metal complex.

5 Claims, 6 Drawing Sheets (a)

(b)

(c)

MOLECULAR ASSEMBLY

BACKGROUND OF THE INVENTION

1. Field of the Invention

The present invention relates to a molecular assembly.

2. Related Background Art

Polymer materials are widely used as general purpose materials and functional materials, including plastics, films, fibers, rubber or coating materials. Crosslinking of polymers by covalent bonds is important for improving the properties of such polymers, such as their strength, heat resistance and recovery from deformation. Such polymer crosslinking has conventionally been carried out with the aim of achieving improved mechanical properties (for example, see Japanese Unexamined Patent Publication No. 2002-239358 and Japanese Unexamined Patent Publication No. 2002-216845), but in recent years there has been increasing interest in the use of crosslinking reactions with the goal of developing functional materials known as "topological gels" that employ polyrotaxane (for example, see Japanese Unexamined Patent Publication No. 2005-320392).

SUMMARY OF THE INVENTION

One strategy that is essential toward creating a society with improved recycling of resources is the development of easily reusable plastics. However, thermoplasticity is sacrificed when linear polymers are crosslinked by covalent bonds to form a three-dimensional network structure, and it is therefore difficult to recover the polymer in molded articles for their reprocessing. It is also difficult, in general, to recover reusable linear polymers by decomposing the covalent bonded crosslinks. A need therefore exists for a method of forming crosslinks without covalent bonds, in order to allow reversible crosslinking between the molecules.

The present invention has been accomplished in light of these circumstances, and its object is to provide a molecular assembly formed by assembling a plurality of molecules by reversible crosslinking.

In order to solve the problems described above, the invention provides a molecular assembly comprising a metal complex with a space formed therein, and compounds having substituents enclosed in the metal complex within the space and molecular chains bonded to the substituents and extending to the exterior of the metal complex, wherein two or more substituents are enclosed in each space of the metal complex.

In the molecular assembly of the invention, two or more substituents are enclosed as guests in the same space of the host metal complex, thus forming an aggregate wherein the molecular chains bonded to each of the substituents are crosslinked via the metal complex. Also, the enclosed substituents can be eliminated from the metal complex by external stimulation, thus allowing reversible disengagement of the crosslinking between molecular chains. The molecular assembly of the invention is formed by assembling a plurality of molecules by reversible crosslinking.

The metal complex in the molecular assembly of the invention is preferably a cage metal complex. This will permit the effect of the invention to be even more effectively exhibited.

The substituents in the molecular assembly of the invention are preferably hydrophobic substituents. Hydrophobic substituents will be more easily enclosed in the space of the metal complex, thus allowing easier control of aggregation/separation of the molecular assembly.

The molecular chains in the molecular assembly of the invention are preferably hydrophilic. Hydrophilic molecular chains will prevent the molecular chain portions from being easily enclosed in the space of the metal complex, thus helping to form a structure with extended molecular chains. Aggregation/separation of the molecular assembly will therefore be even easier to control.

The molecular assembly of the invention preferably forms a network structure with several of the aforementioned metal complexes as crosslinking points. Such a molecular assembly provides a superior material in terms of strength and heat resistance.

DESCRIPTION OF THE PREFERRED EMBODIMENTS

Figure 1:
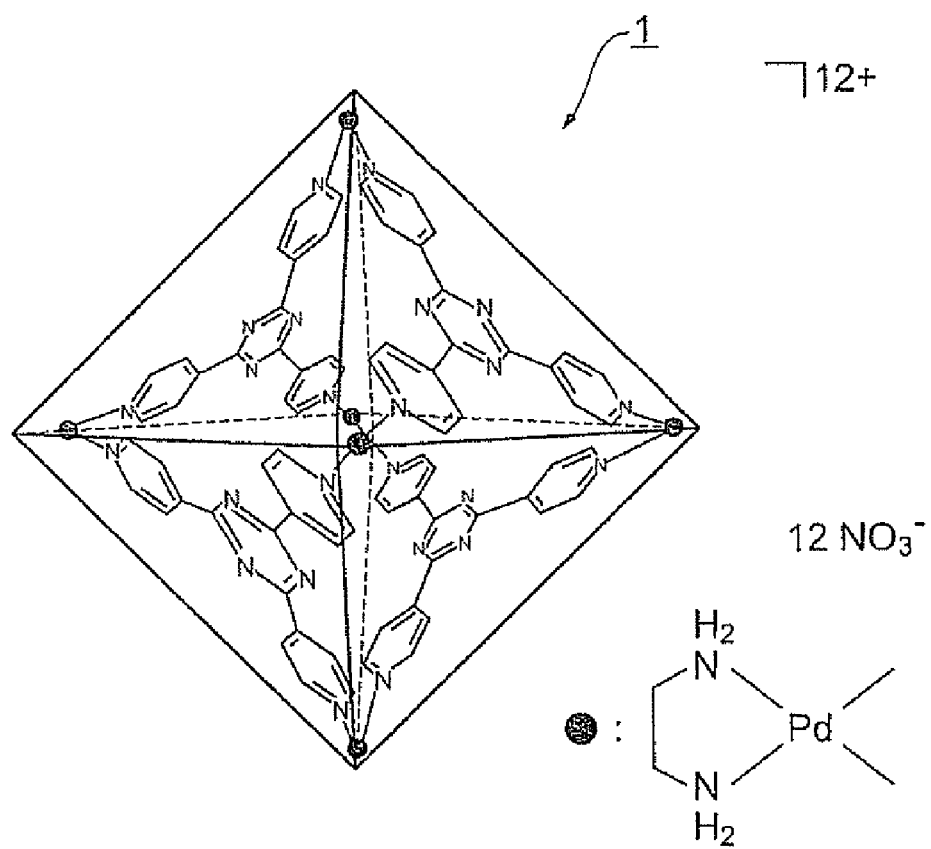
FIG. 1 is a schematic drawing of an embodiment of a cage metal complex.

Preferred embodiments of the invention will now be explained in detail, with reference to the accompanying drawings as necessary. Identical elements in the drawings will be referred to by like reference numerals and will be explained only once. Also, the dimensional proportions depicted in the drawings are not necessarily limitative.

The molecular assembly of the invention comprises a metal complex with a space formed therein (hereinafter also referred to as "host metal complex"), and compounds having substituents enclosed in the metal complex within the space and molecular chains bonded to the substituents and extending to the exterior of the metal complex (hereinafter referred to as "guest compound"). Two or more substituents are enclosed in the same space of the metal complex.

The host metal complex is a metal complex having a transition metal and a ligand coordinated with the transition metal. Shapes of host metal complexes may be classified as cage, bowl, capsule, pillar, tube or sphere shapes. Cage metal complexes are particularly preferred.

FIG. 1 is a schematic drawing of an embodiment of a host metal complex. The host metal complex 1 shown in FIG. 1 is a cage metal complex. The host metal complex 1 is composed of six palladium atoms as the transition metal, with four 2,4,6-tris(4-pyridyl)-1,3,5-triazine and six ethylenediamine molecules as ligands coordinated with the palladium atoms, thus forming an octahedral structure with palladium at each vertex. Inside the octahedral structure there is formed a space enclosing the substituents as guest molecules.

Since 2,4,6-tris(4-pyridyl)-1,3,5-triazine is a ligand with an essentially planar structure, the four 2,4,6-tris(4-pyridyl)-1,3,5-triazine molecules are situated at faces of the octahedron. Two 2,4,6-tris(4-pyridyl)-1,3,5-triazine molecules and one ethylenediamine molecule are arranged at each palladium atom.

The ligands in the host metal complex have electron pairs that can form coordination bonds with the transition metal. Electron pairs include lone electron pairs such as those of nitrogen atoms or oxygen atoms, and π-allyl-based π electron pairs, with lone electron pairs of nitrogen atoms being preferred. As such an electron pair there may be mentioned the electron pair of the nitrogen atom of a pyridine ring, for example. The host metal complex preferably has a plurality of ligands having three or more electron pairs forming coordination bonds with the transition metal, wherein the three or more electron pairs are situated essentially in the same plane (hereinafter referred to as "planar ligands"). More preferably, the planar ligands as a whole form an essentially planar structure.

There are no particular restrictions on the sizes of the planar ligands (the diameters of spheres inscribed within the ligands), but they are usually preferred to be 0.5 nm-5 nm. If the ligand sizes are less than 0.5 nm it will be difficult to form a three-dimensional cage structure, while if the sizes are greater than 5 nm the space in the cage structure will increase, tending to interfere with enclosure of the substituents of the guest compound.

The planar ligands preferably have cyclic structures. As cyclic structures there may be mentioned monocycles, polycycles, fused rings and combinations of such structures. The ligands are more preferably ones wherein the three or more electron pairs forming the coordination bond are arranged in a regular geometric fashion.

More specifically, there may be mentioned ligands having a 6-membered aromatic ring such as a benzene ring or 1,3,5-triazine ring at the center, with an electron pair-containing ring such as a pyridine ring substituting at the 1,3,5-positions or 2,4,6-positions. As specific examples of such planar ligands there may be mentioned 2,4,6-tris(4-pyridyl)-1,3,5-triazine referred to above, or 1,3,5-tris(4-pyridyl)benzene. As a different example, there may be mentioned ligands having a fused ring such as porphin at the center, with 4 pyridine rings substituting at symmetrical positions of the porphin ring.

The host metal complex preferably also has a small ligand separate from the planar ligand. This ligand is preferably sterically anchored to some degree, and most preferably the ligand forms a cyclic structure when coordinated with the center transition metal. As examples of preferred ligands there may be mentioned diamine-based bidentate ligands such as ethylenediamine referred to above.

The transition metal is not restricted to palladium, so long as it is a transition metal that can form a complex by coordination bonding, but platinum or palladium is preferred. There are no particular restrictions on the oxidation state of the transition metal, but from the standpoint of reversibility, it is preferably an oxidized transition metal and more preferably a divalent transition metal.

The host metal complex may be synthesized by reacting a salt or complex of the transition metal with the ligand in a solvent such as water, by a process known to those skilled in the art.

Figure 2:
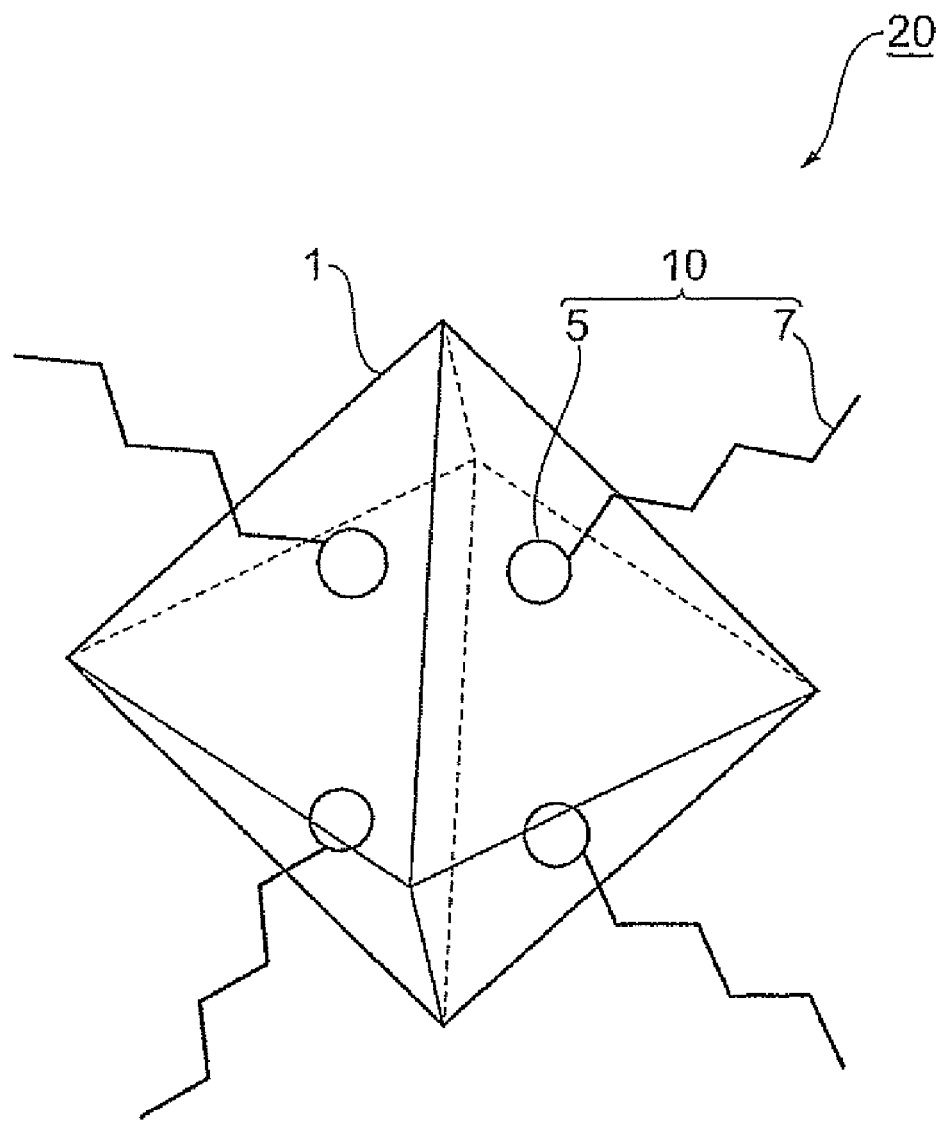
FIG. 2 is a schematic drawing of an embodiment of a molecular assembly.

FIG. 2 is a schematic drawing of an embodiment of a molecular assembly. The molecular assembly 20 shown in FIG. 2 comprises a cage host metal complex 1 according to the embodiment described above, and guest compounds 10 having substituents 5 enclosed in the host metal complex 1 within the space and molecular chains 7 bonded to the substituents 5 and extending to the exterior of the cage metal complex 1. Four substituents 5 are enclosed in the same space of the host metal complex 1. In other words, a plurality of guest compounds 10 are crosslinked via a single host metal complex 1.

The substituents 5 on the guest compounds 10 are hydrophobic substituents, and the substituents 5 are enclosed in the space of the host metal complex 1 primarily by hydrophobic interaction without forming covalent bonds with the host metal complex 1. Thus, the substituents 5 can be easily pulled out of the host metal complex 1 by applying external stimulation. The external stimulation may be, for example, heating or shearing stress.

As examples of hydrophobic substituents there may be mentioned C1-20 alkyl, aromatic and alicyclic groups. Aromatic and alicyclic groups are preferred, with naphthoquinone, cyclopentadienyl, cyclohexadienyl, adamantyl, phenyl, naphthyl, anthranil, pyrenyl, norbomane and fetrocenyl being more preferred and adamantyl being especially preferred.

The molecular chains 7 of the guest compounds 10 are preferably hydrophilic. Thus, when the host metal complex 1 and the guest compounds 10 are mixed in water or a water-soluble solvent, for example, a molecular assembly is rapidly formed in a self-organizing manner, having the substituents 5 enclosed inside the host metal complex 1 and the molecular chains 7 situated outside of the host metal complex 1.

The hydrophilic molecular chains have a partial structure derived from the hydrophilic compounds. As preferred examples of hydrophilic molecular chains there may be mentioned polyethylene oxide chains and polypropylene oxide chains.

As examples of guest compounds there may be mentioned compounds comprising the aforementioned substituents, preferably on the ends of hydrophilic polymers such as polyethylene alcohol, polypropylene alcohol, polyethylene glycol, polypropylene glycol, polyoxyethylenepolyoxy and propylene block copolymer.

Such guest compounds may be synthesized, for example, by reacting a hydroxyl group-containing hydrophilic compound with a halogenated compound such as a hydrophobic substituent-containing acid chloride, by a process known to those skilled in the art.

The molecular assembly of the invention can be easily formed by mixing the host metal complex and the guest compound in a solvent, or by mixing the host metal complex-forming ligand, transition metal and guest compound in a solvent. The solvent used may be water or a water-soluble solvent, although water is preferred.

Figure 3:
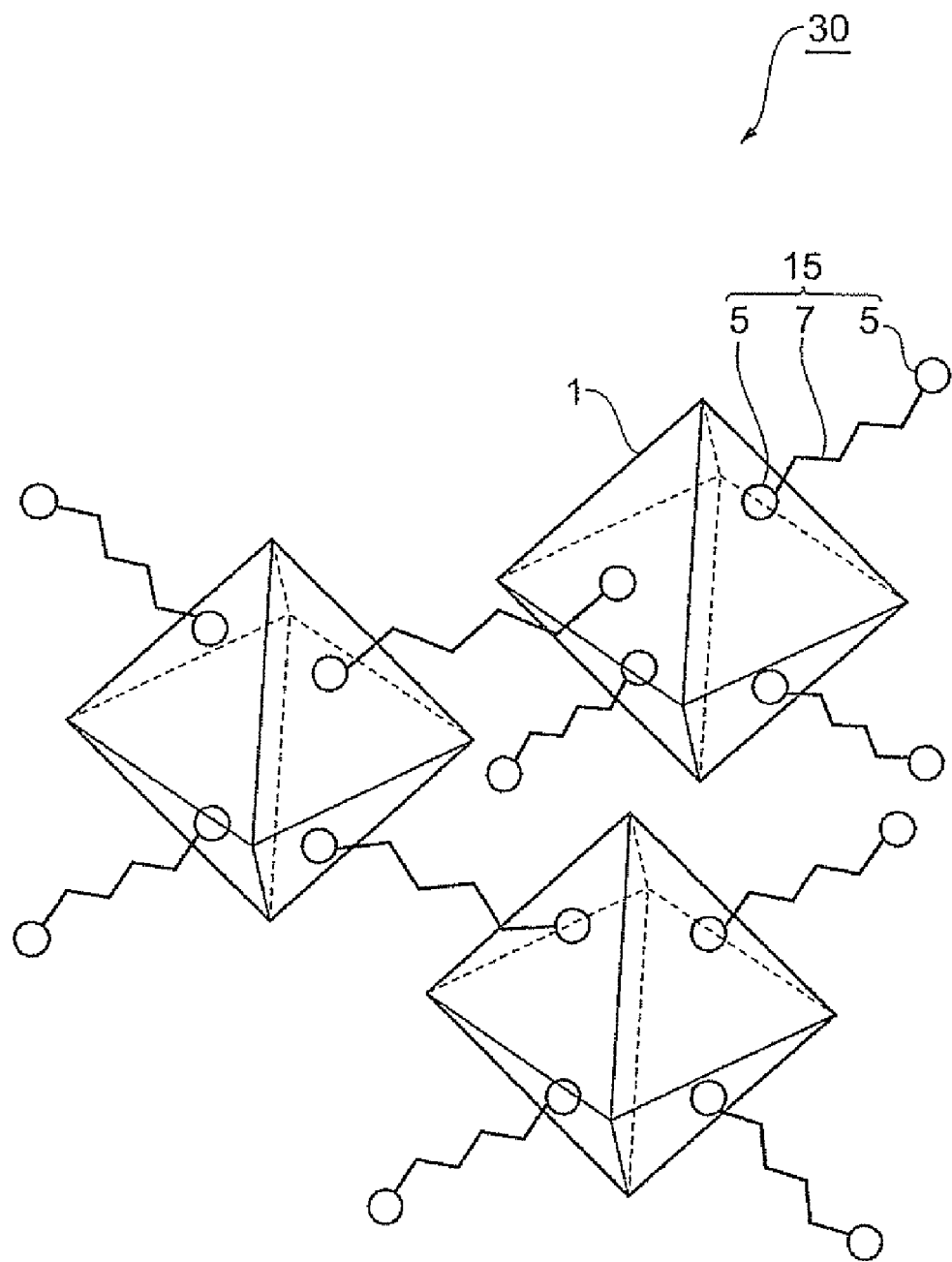
FIG. 3 is a schematic drawing of another embodiment of a molecular assembly.

The molecular assembly of the invention may also have a network structure with host metal complexes as crosslinking points. FIG. 3 is a schematic drawing of another embodiment of a molecular assembly. The molecular assembly 30 shown in FIG. 3 is composed of a plurality of host metal complexes 1 and a plurality of guest compounds 15 having molecular chains 7 and a plurality of substituents 5 bonded to each of the molecular chains 7. The plurality of substituents 5 in the guest compounds 15 are enclosed in separate host metal complexes 1, thereby forming crosslinks between the guest compounds 15 via the host metal complexes 1 so that an overall three-dimensional network structure is formed.

The invention will now be explained in greater detail by the following examples. However, the invention is not limited to the examples described above. The invention may also be applied in a variety of other embodiments so long as the gist thereof is maintained.

EXAMPLES

Preferred examples of the invention will now be explained in further detail. However, the invention is not limited to these examples.

(Measuring Apparatus)

The nuclear magnetic resonance spectra (NMR) were measured using an NM-Lambda50 Superconductive Fourier Transform Nuclear Magnetic Resonance apparatus (trade name of JEOL Corp., 500 MHz). The viscosity ($\eta$) was measured using an RFS-II Fluid Spectrometer (trade name of Rheometrix, Geometry: rotating double cylinder), with a shear rate ($\gamma$) of $10^0$-$10^3$ seconds$^{-1}$ and a temperature of 25±0.1° C.

Synthesis Example 1

In a 10 mL test tube there were placed 60 mg (0.206 mmol) of (en) Pd (II) dinitrate as a transition metal, 43 mg (0.137 mmol) of 2,4,6-tris(4-pyridyl)-1,3,5-triazine as a ligand and 10 mL of water, and the mixture was stirred at room temperature for 24 hours. The insoluble portion was then filtered out and the filtrate was concentrated with an evaporator, to obtain 98.7 mg of a light-yellow solid cage metal complex (Pd-Cage) (yield: 97%). The NMR of the obtained cage metal complex was measured to identify its structure.

$^1$H-NMR (500 MHz, D$_2$O) δ 9.16 (d, 2H, Ar—H), 8.66 (d, 2H, Ar—H), 3.00 (d, 2H, —NCH$_2$CH$_2$N).

Synthesis Example 2

In a 100 mL round-bottomed flask there were placed 4.4 g (22.0 mmol) of 1-adamantanecarbonyl chloride and 30 mL of tetrahydrofuran. After then adding 1.5 g (10.0 mmol) of triethylene glycol, 4.1 mL (30.0 mmol) of triethylamine was added dropwise to produce a white precipitate. The mixture was stirred at 26° C. for 5 hours and then filtered with a Kiriyama funnel, after which 50 mL of 10% hydrochloric acid was added to the filtrate and extraction was performed with ethyl acetate. The organic layer was dried over sodium sulfate, and after concentration, it was purified by column chromatography (hexane/ethyl acetate=3/1, hexane/ethyl acetate=1/1) to obtain 4.16 g of the compound (Ad-tri-Ad) represented by the following formula (1) (yield: 40%). The $^1$H-NMR of the obtained compound was measured to identify its structure.

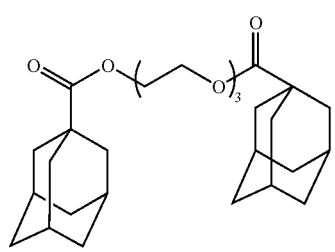

(1)

Synthesis Example 3

The same procedure was carried out as in Synthesis Example 2 using 1.94 g (10.0 mmol) of tetraethylene glycol instead of triethylene glycol, to obtain 4.00 g of the compound (Ad-tetra-Ad) represented by the following formula (2) (yield: 68%). The $^1$H-NMR of the obtained compound was measured to identify its structure.

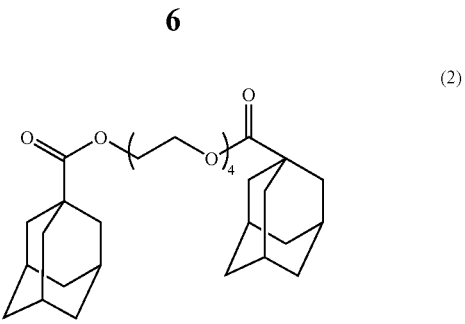

(2)

Example 1

After placing the cage metal complex obtained in Synthesis Example 1 (Pd-Cage, 29.9 mg, 10.0×10$^{-3}$ mmol) and the adamantyl group-containing guest compound synthesized in Synthesis Example 2 (Ad-tri-Ad, 10.0×10$^{-2}$ mmol, 10 equivalents) in a test tube, 1 mL of deuterated water was added and the mixture was stirred to prepare an aqueous solution of a molecular assembly.

Example 2

The procedure of Example 1 was carried out, except for using the adamantyl group-containing guest compound (Ad-tetra-Ad) synthesized in Synthesis Example 3 instead of Ad-tri-Ad, to produce an aqueous solution of a molecular assembly.

Comparative Example 1

The same procedure was carried out as in Example 1 but without using an adamantyl group-containing compound, to produce an aqueous solution of a cage metal complex.

Comparative Example 2

The same procedure was carried out as in Example 1 but without using a cage metal complex, to produce an aqueous solution of Ad-tri-Ad.

Comparative Example 3

The same procedure was carried out as in Example 2 but without using a cage metal complex, to produce an aqueous solution of Ad-tetra-Ad.

<External Observation>

In order to examine how the adamantyl groups were enclosed in the cage metal complex, the aqueous solutions prepared in the examples and comparative examples were allowed to stand at room temperature for 10 minutes, and the changes after standing were visually observed. Since Comparative Examples 2 and 3 had no cage metal complexes, the compounds precipitated and failed to dissolve or disperse in water, whereas Examples 1 and 2 dispersed in water even after standing. This confirmed that the adamantyl groups of the compounds had become enclosed in the cage metal complexes.

<NMR Measurement>

Figure 4:
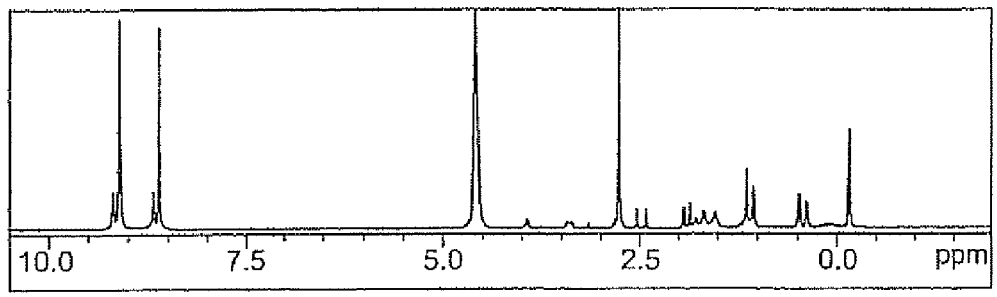
FIG. 4 shows (a) an NMR spectrum of the molecular assembly of Example 1, (b) an NMR spectrum of the Ad-tri-AD aqueous solution of Comparative Example 2, and (c) an NMR spectrum of the cage metal complex aqueous solution of Comparative Example 1.
Figure 4:
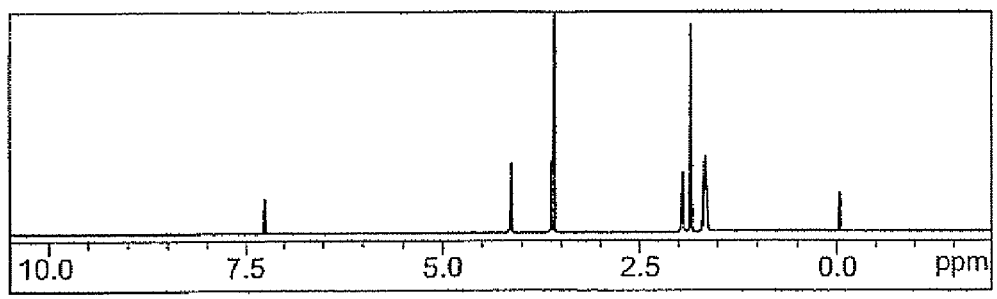
Figure 4:
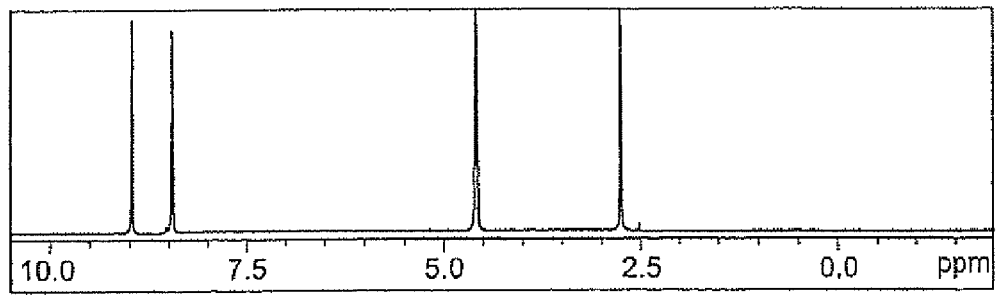

In order to examine enclosure of the adamantyl groups in the cage metal complexes, the aqueous solutions prepared in Example 1 and Comparative Examples 1 and 2 were subjected to NMR measurement and compared. FIG. 4(a) shows the NMR spectrum for the molecular assembly prepared in Example 1, FIG. 4(b) shows the NMR spectrum for the cage metal complex, and FIG. 4(c) shows the NMR spectrum for Ad-tri-Ad. When FIGS. 4(a) and (b) are compared, the aqueous solution of the molecular assembly of Example 1 shows a shift in the peak for the guest compound Ad-tri-Ad toward the upfield end. In most cases where a molecule is incorporated inside another molecule, the NMR spectrum of the incorporated molecule is known to be shifted toward the upfield end with respect to its ordinary state, (see Angew. Chem. Int. Ed., 37, 3142(1998), Angew. Chem. Int. Ed., 39, 4119(2000)). This result therefore provided confirmation that the adamantyl groups in the guest compound had become enclosed in the cage metal complexes.

<Viscosity Measurement>

Figure 5:
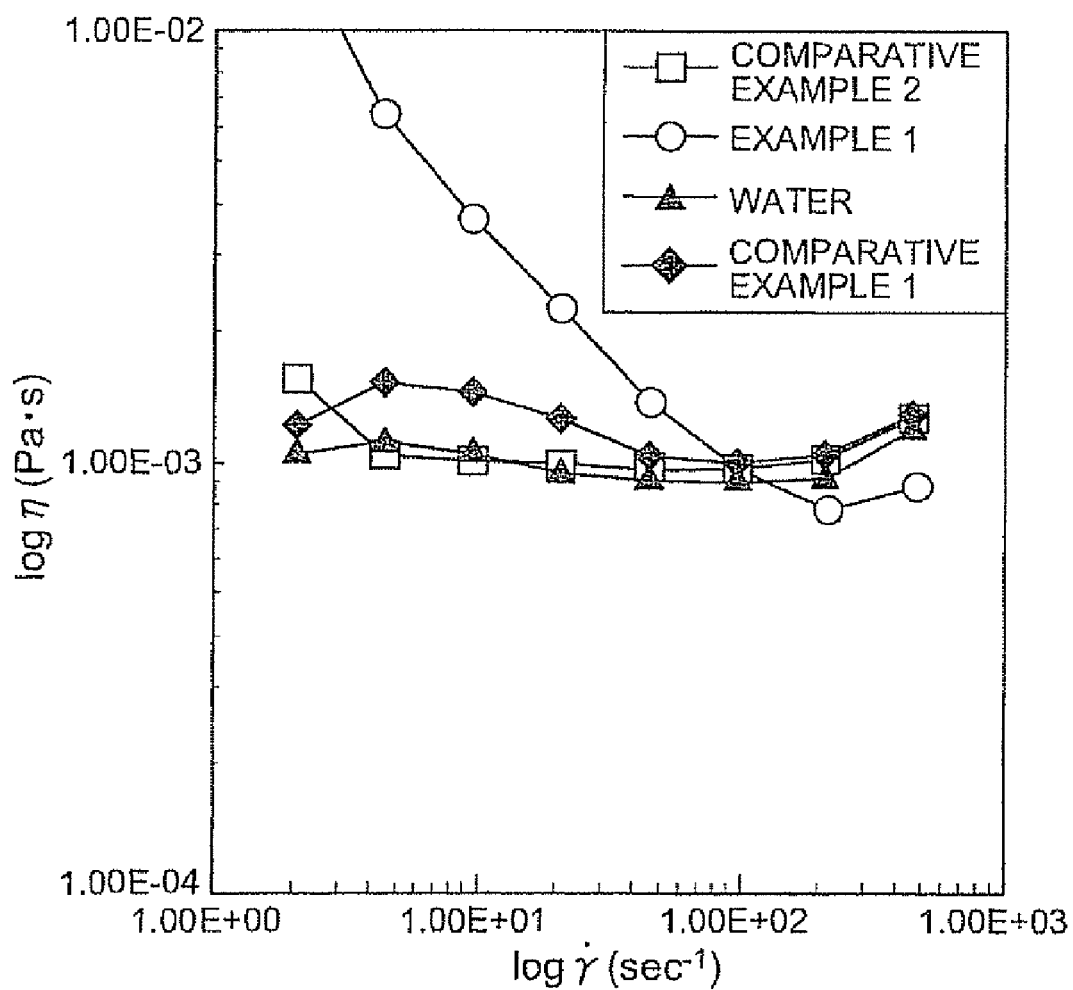
FIG. 5 is a graph showing the relationship between shear rate and viscosity.
Figure 6:
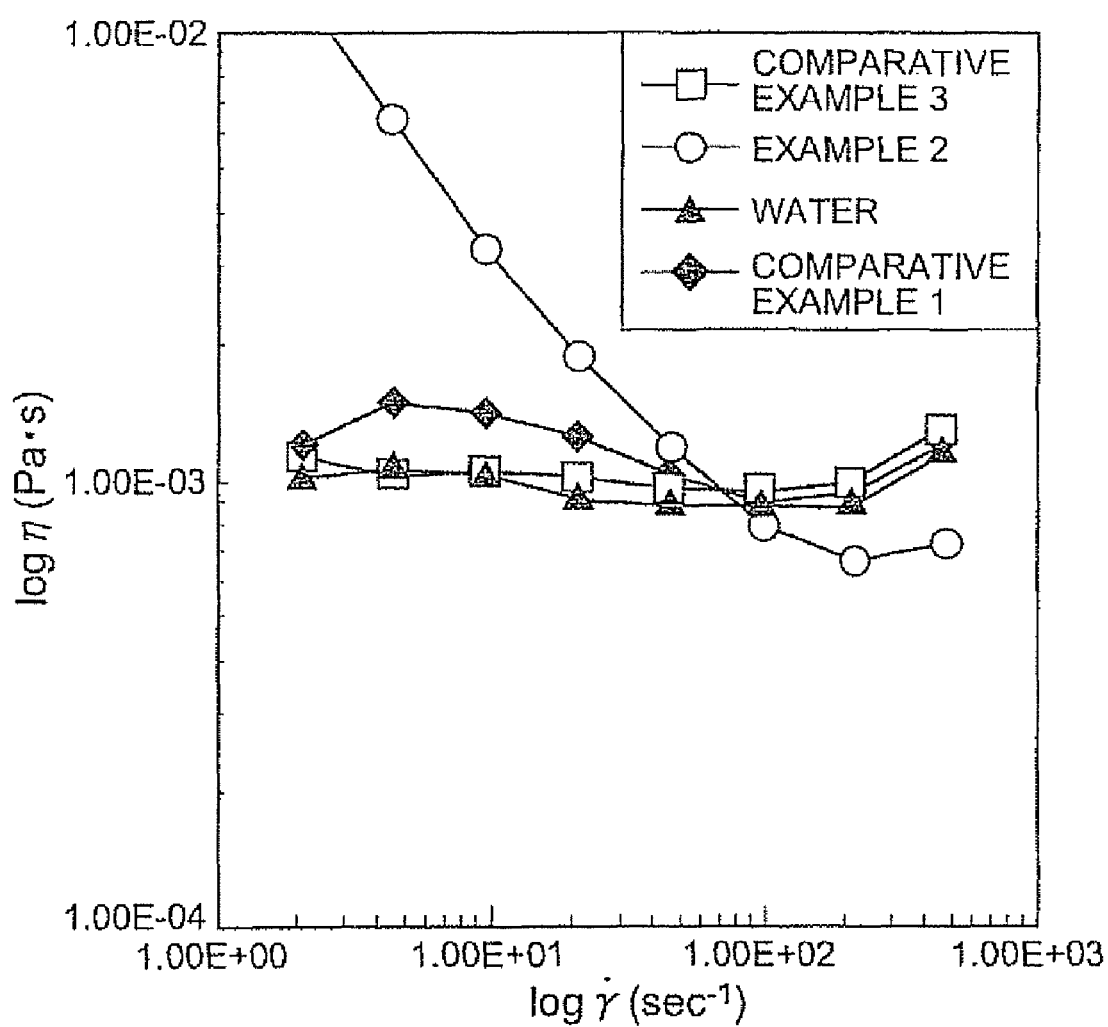
FIG. 6 is a graph showing the relationship between shear rate and viscosity.

The relationship between shear rate and viscosity for the aqueous solutions of the molecular assemblies prepared in Examples 1 and 2 were measured and compared against the comparative examples (the compound alone and the cage metal complex alone). FIG. 5 shows the relationship between shear rate and viscosity for the aqueous solution of the molecular assembly of Example 1, and FIG. 6 shows the relationship between shear rate and viscosity for the aqueous solution of the molecular assembly of Example 2. The aqueous solutions of the molecular assemblies prepared in Examples 1 and 2 had lower viscosities with increasing shear rate, thus exhibiting thixotropic viscosity behavior This suggests that enclosure of the adamantyl groups in the cage metal complex was reversible by applying shearing stress. This also serves as an application example, confirming that the molecular assembly of the invention is useful as a functional material for flow property control.

Thus, since the molecular assembly of the invention is formed as an assembly of a plurality of molecules by reversible crosslinking, molecular aggregation/separation can be reversibly controlled by external stimulation. The molecular assembly of the invention can therefore be utilized as a recycling material, as a sol-gel conversion material (a coating material, oil, dispersing agent flow property adjustor or the like) or a stimulation-responding material (molecular switch, molecular sensor or the like).

According to the invention it is possible to provide a molecular assembly formed by assembling a plurality of molecules by reversible crosslinking. This allows a reversible three-dimensional network structure to be formed by reversible crosslinking, for utilization as a material that is readily reusable while having a network structure that is advantageous in terms of strength and heat resistance.

What is claimed is:

1. A molecular assembly comprising:
    a metal complex with a space formed therein, the metal complex comprising a transition metal and a ligand; and
    compounds having substituents enclosed in the metal complex within the space and molecular chains bonded to the substituents and extending to the an exterior of the metal complex,
    wherein:
        two or more substituents are enclosed in the same space of the metal complex;
        the transition metal is palladium; and
        the ligand comprises:
            a diamine-based bidentate ligand; and
            a planar ligand selected from the group consisting of:
                2,4,6-tris(4-pyridyl)-1,3,5-triazine, and
                1,3,5-tris(4-pyridyl)benzene.

2. A molecular assembly according to claim 1, wherein the metal complex is a cage metal complex.

3. A molecular assembly according to claim 1, wherein the substituents are hydrophobic substituents.

4. A molecular assembly according to claim 1, wherein the molecular chains are hydrophilic.

5. A molecular assembly according to claim 1, which forms a network structure with several of the metal complexes as crosslinking points.

* * * * *